United States Patent
Voorhees

(10) Patent No.: US 7,556,612 B2
(45) Date of Patent: Jul. 7, 2009

(54) DUAL-LUMEN BI-DIRECTIONAL FLOW CATHETER

(75) Inventor: Earl Voorhees, Warrington, PA (US)

(73) Assignee: Medical Components, Inc., Harleysville, PA (US)

( * ) Notice: Subject to any disclaimer, the term of this patent is extended or adjusted under 35 U.S.C. 154(b) by 509 days.

(21) Appl. No.: 10/969,278

(22) Filed: Oct. 20, 2004

(65) Prior Publication Data

US 2005/0085765 A1 Apr. 21, 2005

Related U.S. Application Data

(60) Provisional application No. 60/513,178, filed on Oct. 20, 2003.

(51) Int. Cl.
*A61M 3/00* (2006.01)
*A61M 5/00* (2006.01)
(52) U.S. Cl. .......................... 604/43; 604/264
(58) Field of Classification Search .................. 604/43, 604/264, 523–533, 284, 537, 96.01, 101.01–103.14; 606/191–194
See application file for complete search history.

(56) References Cited

U.S. PATENT DOCUMENTS

| | | | | |
|---|---|---|---|---|
| 4,451,252 A | * | 5/1984 | Martin | 604/43 |
| 4,643,711 A | * | 2/1987 | Bates | 604/6.16 |
| 4,753,640 A | * | 6/1988 | Nichols et al. | 604/247 |
| 5,057,073 A | * | 10/1991 | Martin | 604/43 |
| 5,167,623 A | | 12/1992 | Cianci et al. | |
| 5,219,335 A | * | 6/1993 | Willard et al. | 604/103.05 |
| 5,221,256 A | | 6/1993 | Mahurkar | |
| 5,378,230 A | | 1/1995 | Mahurkar | |
| 5,380,276 A | * | 1/1995 | Miller et al. | 604/28 |
| 5,437,637 A | | 8/1995 | Lieber et al. | |
| 5,486,159 A | | 1/1996 | Mahurkar | |
| 5,556,390 A | * | 9/1996 | Hicks | 604/523 |
| 5,868,717 A | * | 2/1999 | Prosl | 604/264 |
| 5,968,009 A | * | 10/1999 | Siman | 604/43 |
| 5,976,103 A | * | 11/1999 | Martin | 604/43 |
| 6,572,610 B2 | * | 6/2003 | Kovalcheck et al. | 606/21 |
| 6,576,001 B2 | * | 6/2003 | Werneth et al. | 607/104 |

* cited by examiner

*Primary Examiner*—Kevin C Sirmons
*Assistant Examiner*—Andrew M Gilbert
(74) *Attorney, Agent, or Firm*—Anton P. Ness; Fox Rothschild LLP

(57) ABSTRACT

A multi-lumen catheter assembly (100) including an elongated cannulating body (102) having a generally circular cross-section. The body includes a first lumen (110) having a generally arcuate cross-section with a generally rounded first cross-section end and a generally rounded second cross-section end. The body (102) further includes a second lumen (112) having a generally oblong cross-section extending in a radial direction and having a first end (112*a*), a second end (112*b*) and a major axis (128) extending between the first end and the second end and that bisects the arcuate cross-section of the first lumen (110), wherein at least a portion of the first end (112*a*) of the second lumen (112) is disposed between the first generally rounded cross-section end (110*a*) and the second generally rounded cross-section end (110*b*).

21 Claims, 3 Drawing Sheets

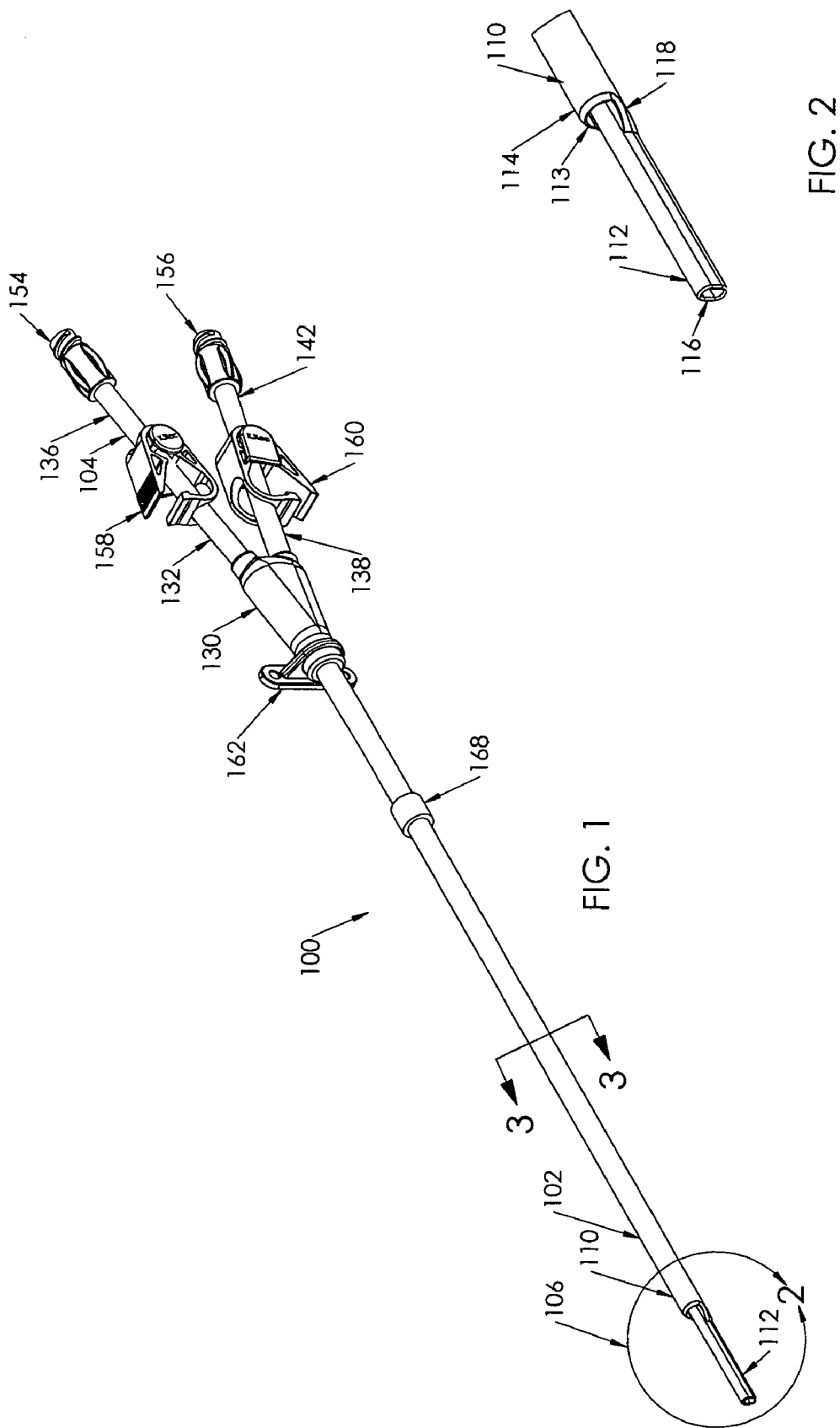

DUAL-LUMEN BI-DIRECTIONAL FLOW CATHETER

CROSS REFERENCE TO RELATED APPLICATION

The present application claims the benefit of U.S. Provisional Patent Application Ser. No. 60/513,178 filed on Oct. 20, 2003.

FIELD OF THE INVENTION

The present invention relates to a multi-lumen catheter with improved fluid flow through the catheter lumens.

BACKGROUND OF THE INVENTION

Catheters for the introduction or removal of fluids may be located in various venous locations and cavities throughout the body of a patient for introduction of fluids to the body or removal of fluids from the body. Such catheterization may be performed by using a single catheter having multiple lumens. A typical example of a multiple lumen catheter is a dual lumen catheter assembly in which one lumen introduces fluid and the other lumen removes fluid. An example of such a dual lumen catheter assembly is the SPLIT-CATH® catheter.

Generally, to insert any catheter into a blood vessel, the vessel is identified by aspiration with a long hollow needle in accordance with the well known Seldinger technique. When blood enters a syringe attached to the needle, indicating that the vessel has been found, a thin guidewire is then introduced, typically through a syringe needle or other introducer device into the interior of the vessel. The introducer device is then removed, leaving the guidewire within the vessel. The guidewire projects beyond the surface of the skin. At this point, several options are available to a physician for catheter placement. The simplest is to pass a catheter into the vessel directly over the guidewire. The guidewire is then removed, leaving the catheter in position within the vessel. However, this technique is only possible in cases where the catheter (for example, a small diameter dual lumen catheter) is of a relatively small diameter, made of a stiff material, and not significantly larger than the guidewire. If the catheter to be inserted is significantly larger than the guidewire, a dilator device with a sheath is passed over the guidewire to enlarge the opening in the vessel. The guidewire and dilator are then removed, leaving the sheath in position within the vessel. The catheter is then passed through the sheath into the vessel, and the sheath is removed by tearing the sheath and pulling the sheath out of the vessel around the catheter.

However, the designs of some existing multi-lumen catheters may induce turbulent flow through the catheter lumens, resulting in localized regions of reduced blood flow through the catheter lumens and a potential for the formation of blood clots in or near these regions within the catheter lumens. Also, some multi-lumen catheter designs have a lumen cross-sectional shape that allows blood clotting around the exterior of the catheter lumens within the patient's blood vessel. It would be beneficial to provide a multi-lumen catheter with improved flow capability and which decreases the likelihood of blood clotting within the catheter lumens or around the exterior of the catheter.

BRIEF SUMMARY OF THE INVENTION

Briefly, the present invention provides a multi-lumen catheter assembly comprising a first lumen having a generally arcuate cross-section with a first cross-section end and a second cross-section end and a second lumen having a generally oblong cross-section. The generally oblong cross section of the second lumen comprises a first end, a second end and a major axis extending therethrough, between the first end and the second end and extends in a radial direction and bisectss the arcuate cross-section of the first lumen. At least a portion of the first end of the second lumen is disposed between the first cross-section end and the second cross-section end.

Additionally, the present invention provides a multi-lumen catheter assembly that includes an elongated cannulating body having a generally circular cross-section. The body includes a first lumen having a generally arcuate cross-section with a generally rounded first cross-section end and a generally rounded second cross-section end. The body further includes a second lumen having a generally oblong cross-section that comprises a first end, a second end and a major axis extending therethrough, between the first end and the second end and extends in a radial direction and bisects the arcuate cross-section of the first lumen. At least a portion of the first end of the second lumen is disposed between the first generally rounded end and the second generally rounded cross-section end.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIG. 1 is a perspective view of a catheter assembly according to a first preferred embodiment of the present invention.

FIG. 2 is an enlarged perspective view of a distal tip of the catheter assembly shown in FIG. 1.

DETAILED DESCRIPTION OF THE INVENTION

Figure 5:
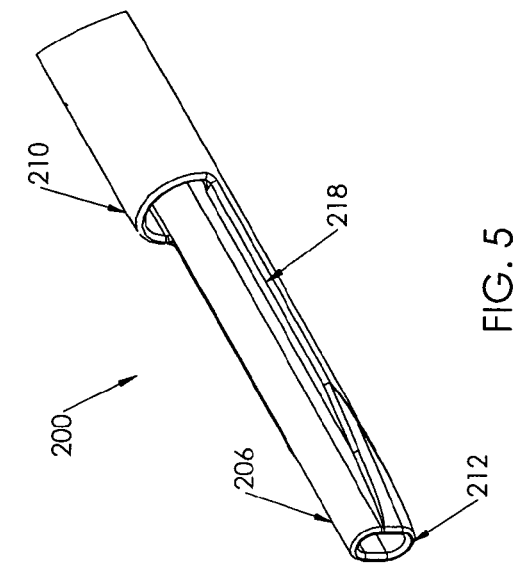
FIG. 5 is an enlarged perspective view of a distal tip of a catheter assembly according to a second preferred embodiment of the present invention.

In the drawings, like numerals indicate like elements throughout. Certain terminology is used herein for convenience only and is not to be taken as a limitation on the present invention. The words "proximal" and "distal" refer to directions away from and closer to, respectively, the insertion tip of the catheter in the catheter assembly according to the present invention. The terminology includes the words above specifically mentioned, derivatives thereof, and words of similar import. The following describes preferred embodiments of the invention. However, it should be understood based on this disclosure, that the invention is not limited by the preferred embodiments described herein.

Referring to FIG. 1, a catheter assembly 100 according to a first embodiment of the present invention is shown. The catheter assembly 100 includes a cannulating portion 102 that is inserted through an incision and into a blood vessel of a patient (not shown), and an extension portion 104 that remains exterior of the body of the patient. The cannulating portion 102 includes a distal end 106 having a first lumen 110 and a second lumen 112.

For the purposes of describing the preferred embodiment of the present invention, the device will be described with respect to the preferred application of hemodialysis, more specifically, for purifying blood flowing through the internal jugular vein of the patient. However, it will be understood by one skilled in the art based on this disclosure, that the catheter assembly 100 may be configured and adapted, by increasing or decreasing the catheter size and/or number of catheters and/or lumens in the assembly, such that the catheter assembly 100 may be beneficially used for other medical applications in which fluids are introduced into and/or removed from the body.

The catheter assembly 100 of the present invention may be adapted for use in various applications in which bodily fluids, medicaments or other solutions are introduced into and removed from the body such as perfusion, infusion, plasmapheresis, hemodialysis, chemotherapy, and the like. The area to be catheterized is preferably a blood vessel such as an internal jugular vein, but may be any suitable area within the body. Other areas in which the catheter assembly may be used include, for example, other blood vessels, including the femoral and subclavian veins, any abscess cavity, post-operative cavity, the peritoneal cavity, and other areas of the body including intra-abdominal, sub-diaphragmatic and sub-hepatic areas. It should be understood by one of ordinary skill in the art from this disclosure that these areas are exemplary, and that the catheter assembly 100 may be used to remove or introduce fluids in various areas to be catheterized.

The catheter assembly 100 as shown in FIG. 1 is preferably useful for intake, or removal, of blood to be purified from a blood vessel, such as the internal jugular vein, and introduction of purified blood into the same vessel. The blood may be purified by any suitable hemodialysis apparatus (not shown) attached in communication with the lumens of the catheter assembly 100. The catheters may also be used to introduce medication or other fluids including glucose or saline solutions into the body.

Figure 4:
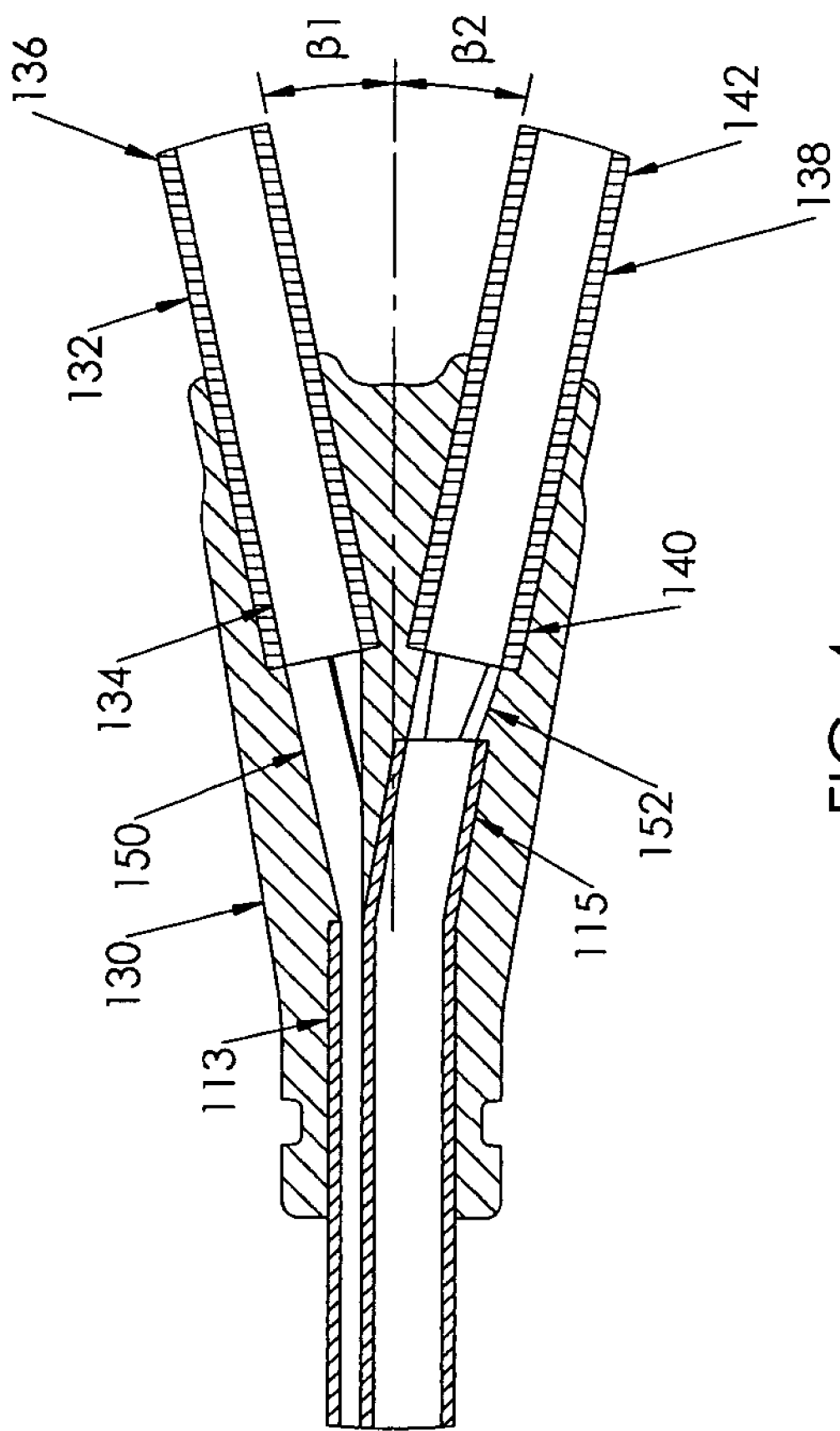
FIG. 4 is an enlarged sectional view of a hub for the catheter assembly of FIG. 1.

An enlarged sectional view proximate to the distal end 106 of the catheter assembly 100 is shown in FIG. 2. As can be seen from FIGS. 2 and 4, the first lumen 110 has a first proximal end 113 and a first distal tip 114. The second lumen 112 has a second proximal end 115, as can be seen in FIG. 4, and a second distal tip 116 that, as can be seen in the enlarged FIG. 2, extends a distance distally of the first distal tip 114. Preferably, the distance between the first distal tip 114 and the second distal tip 116 is approximately 2.5centimeters, although those skilled in the art will recognize that the distance between the first distal tip 114 and the second distal tip 116 may be more or less than 2.5centimeters. The first distal tip 114 of the first lumen 110 in the first embodiment preferably ends in a plane generally perpendicular to the length of the cannulating portion 102. A support rib 118 is seen to be defined along each side of the distal tip portion of the second lumen 112 and extending laterally outwardly therefrom, and extends from the first distal tip 114 of the first lumen 110 toward the second distal tip 116 of the second lumen 112, thus being external of both lumens. The support rib 118 tapers inward toward the second lumen 112 to provide a smooth transition between the second lumen 112 and the first lumen 110. The support rib 118 provides additional stability between the first lumen 110 and the second lumen 112, thereby restricting the first lumen 110 from collapsing about the second lumen 112 during use.

Figure 3:
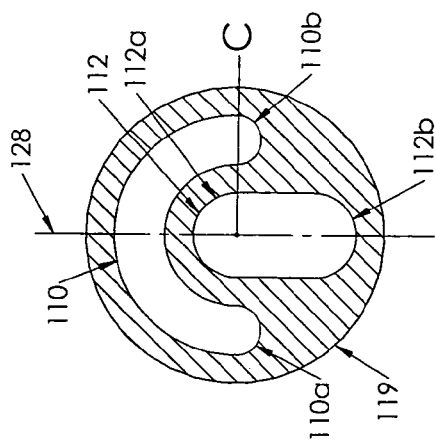
FIG. 3 is an enlarged sectional view of the catheter assembly of FIG. 1, taken along lines and arrows 3-3 of FIG. 1.

As is further seen in FIG. 3, preferably, the cannulating portion 102 of the catheter assembly 100 has a circular body 119, with a geometric center C. The circular cross-section of the body 119 provides a smooth engagement with the incision through which the cannulating portion 102 of the catheter assembly 100 is inserted to reduce risk of the patient bleeding through the incision while the catheter assembly 100 is in the patient. Further, the circular cross-section 119 reduces the likelihood of blood clotting along the exterior of the cannulating portion 102 that has been inserted into the patient's blood vessel.

The first and second lumens 110, 112 are disposed wholly within the circular body 119. The first lumen 110 has a generally arcuate, and preferably, generally semi-annular shape, with a first generally rounded end 110a and a second generally rounded end 110b. Preferably, the generally semi-annular shape extends at least 180 degrees. The second lumen 112 has a generally oblong shape, having first and second ends and first and second elongated opposing sides. A first end 112a of the second lumen 112 is disposed between the first generally rounded end 110a and the second generally rounded end 110b of the first lumen 110. Preferably, the geometric center C is disposed within the first end 112a of the second lumen 112. A second end 112b of the second lumen 112 is disposed proximate to the surface of the cannulating portion 102. The oblong cross-sectional shape of the second lumen 112 has a major axis extending parallel to the elongated onposing sides, and between the first and second ends, and is oriented radially with respect to the catheter, with the generally long dimension of the oblong extending radially from the center of the catheter C and away from the central portion of the arcuate first lumen 110, and the major axis 128 of the second lumen 112 extends in a radial direction and generally bifurcates the first lumen 110 and the second lumen 112. Preferably, the first and second ends 110a, 110b of the first lumen 110 and the first and second ends 112a, 112b of the second lumen 112 are generally rounded to reduce areas of low fluid flow through the lumens 110, 112, and to reduce the risk of blood clotting within the lumens 110, 112.

Preferably, a ratio of the hydraulic radius of the second lumen 112 to the hydraulic radius of the first lumen 110 is between approximately 1.16 and 1.31. Also preferably, a ratio of the equivalent diameter ratio of the second lumen 112 to the first lumen 110 is between approximately 0.77 and 0.85. Further, a ratio of the cross-sectional area of the second lumen 112 to the cross-sectional area of the first lumen 110 is between approximately 0.606 and 0.731. Those skilled in the art will recognize that the ratios disclosed herein are optimum ratios and that these ratios may vary outside of the given scopes without exceeding the scope of the present invention.

Referring back to FIG. 1, the catheter assembly 100 includes a hub 130, disposed along the catheter assembly 100, generally between the cannulating portion 102 and the extension portion 104. Referring to FIG. 4, the hub 130 and extension tubes 132, 138 are now explained in detail. However, it should be understood, based on this disclosure that a hub 130 and extension portion 104 of the catheter assembly 100 is optional. The proximal ends 113, 115 of the first and second lumens 110, 112, respectively, may be made to be directly connectable to dialysis equipment or other apparatus by providing luers or other connectors to the proximal ends 113, 115 of the first and second lumens 110, 112, respectively, without the hub 130 or additional extension tubes. In the preferred embodiment as shown, however, such hub 130 and extension tubes 132, 138 are provided and are described below.

As discussed above, the cannulating portion 102 of the catheter assembly 100 is preferably joined to the extension portion 104 in the hub 130. As shown in FIG. 1 and in the enlarged sectional view of the hub 130 in FIG. 4, the extension portion 104 includes a first extension tube 132 having a first distal end 134 and a first proximal end 136, and a second extension tube 138 having a second distal end 140 and a second proximal end 142. The extension tube distal ends 134, 140 and the respective proximal ends 113, 115 of the catheters 10, 112 are brought into fluid communication with each other via first and second tunnels 150, 152 molded in the hub 130.

The first tunnel 150 is preferably generally circular in cross section proximate to the first extension tube 132 to facilitate a smooth fluid transition between the first extension tube 132 and the tunnel 150, and becomes preferably generally arcuate in cross section proximate to the first lumen 110 to facilitate a smooth fluid transition between the first extension tube 132 and the first lumen 110. The second tunnel 152 is preferably generally circular in cross section proximate to the second extension tube 138 to facilitate a smooth fluid transition between the second extension tube 138 and the second tunnel 152, and becomes preferably generally oblong in cross section proximate to the second lumen 112 to facilitate a smooth fluid transition between the second extension tube 138 and the second lumen 112. As can be seen in FIG. 4, the first tunnel 150 bends at an angle $\beta_1$ of approximately 12 degrees between the first lumen 110 and the first extension tube 132 and the proximal end 115 of the second lumen 112 bends at an angle $\beta_2$ of approximately 12 degrees. The slight bending angles $\beta_1$, $\beta_2$ of approximately 12 degrees provide gradual deflection of the fluid flowing through the catheter assembly 100 that minimizes turbulent fluid flow within the lumens 110, 112, the first and second tunnels 150, 152, and the extension tubes 132, 138.

Referring back to FIG. 1, the proximal ends 136, 142 of the extension tubes 132, 138 are preferably connected to respective luer locks 154, 156 in a conventional manner. If desired, the luer locks 154, 156 may be substituted with any suitable type of quick connect fittings, ferrule connectors, threadable connector, and the like. A clamp 158, 160 may be disposed over each extension tube 132, 138 between the hub 130 and each luer lock 154, 156, respectively, in order to be able to releasably restrict fluid flow through each respective lumen 110, 112.

Accordingly, the first and second lumens 110, 112 are in fluid communication with respective first and second extension tubes 132, 138. The hub 130 preferably includes a suture wing 162 for securing the catheter assembly 100 to the patient, if desired, for example for acute catheterizations.

An ingrowth cuff 168 is disposed on the exterior of the cannulating portion 102 between the hub 162 and the distal end 110. The ingrowth cuff 168 is preferably constructed from a fiber, preferably a polyester, such as DACRON® polyester, or other suitable material. The catheter assembly 100 is preferably inserted into the patient sufficiently far so that the ingrowth cuff 168 is disposed subcutaneously within the patient. The patient's skin tissue grows into and around the material comprising the ingrowth cuff 168, securing the ingrowth cuff 168 and the entire catheter assembly 100 to the patient.

In one preferred embodiment of the present invention, the cannulating portion 102 of the catheter assembly 100 is fabricated by a single extrusion process, injection molding process, or blow molding process. The preferred fabrication process is extrusion.

This catheter assembly 100 is designed to function efficiently with new and effectively higher flow rate dialysis devices, which have flow rates of about 450 cc/min, with operating pressures of up to approximately 13.8 bars (200 psi). The ability to use higher flow rates without collapse of the lumens, as in multiple lumen catheters, decreases the time necessary for a patient to undergo conventional dialysis treatments, thereby providing a significant benefit to the patient.

Preferably, the first and second lumens 110, 112 are constructed from CARBOTHANE™ polyurethane, with approximately 20% barium sulfate to provide radiopacity, although those skilled in the art will recognize that other, suitable biocompatible material may be used. For example, the first and second lumens 110, 112 may be made of a biocompatible plastic or elastomer, more preferably from a biocompatible elastomer. Suitable biocompatible plastics include materials such as, for example, polyethylene, homopolymers and copolymers of vinyl acetate such as ethylene vinyl acetate copolymer, polyvinylchlorides, homopolymers and copolymers of acrylates such as polymethylmethacrylate, polyethylmethacrylate, polymethacrylate, ethylene glycol dimethacrylate, ethylene dimethacrylate and hydroxymethyl methacrylate, polyurethanes, polyvinylpyrrolidone, 2-pyrrolidone, polyacrylonitrile butadiene, polycarbonates, polyamides, fluoropolymers such as homopolymers and copolymers of polytetrafluoroethylene and polyvinyl fluoride, polystyrenes, homopolymers and copolymers of styrene acrylonitrile, cellulose acetate, homopolymers and copolymers of acrylonitrile butadiene styrene, polymethylpentene, polysulfones, polyesters, polyimides, polyisobutylene, polymethylstyrene and other similar compounds known to those skilled in the art. It should be understood that these possible biocompatible polymers are included above for exemplary purposes and should not be construed as limiting. If a biocompatible polymeric material is used to form the first and second lumens 110, 112, it is preferred that the polymeric material includes a polyurethane or a polyolefin polymeric material having a preferably soft durometer, as specified below.

Suitable, preferred, biocompatible elastomers for use in forming the first and second lumens 110, 112 include biocompatible elastomers such as medical grade silicone rubbers, polyvinyl chloride elastomers, polyolefin homopolymeric and copolymeric elastomers, urethane-based elastomers, and natural rubber or other synthetic rubbers. Preferably, the first and second lumens 110, 112 are made of the elastomeric material such that they are flexible, durable, soft, and easily conformable to the shape of the area to be catheterized in the patient and minimize risk of harm to vessel walls. If the first and second lumens 110, 112 are used for hemodialysis applications, they are preferably formed of a soft silicone elastomer which has a hardness of at least about 80-A and preferably about 85-A on a Shore durometer scale. Such an elastomer is available from Dow Corning, and may include 20% barium sulfate in the elastomer to provide radiopacity. While it is preferred to have a higher Shore durometer hardness if a biocompatible elastomer is used, particularly for hemodialysis, it is also possible to make a device from an elastomer having a lower Shore durometer hardness without departing from the spirit of the invention. It will be understood, based on this disclosure, that the first and second lumens 110, 112 may also be radiopaque depending on their intended use.

A second embodiment of a distal end 206 of a catheter assembly 200 according to the present invention is shown in FIG. 5. The distal end 206 of the catheter assembly 200 is similar to the distal end 106 of the catheter assembly 100 as described above with respect to the first embodiment of the present invention, but includes a support rib 218 that extends from a first lumen 210 to a second lumen 212, tapering from the first lumen 210 to the second lumen 212.

Figure 6:
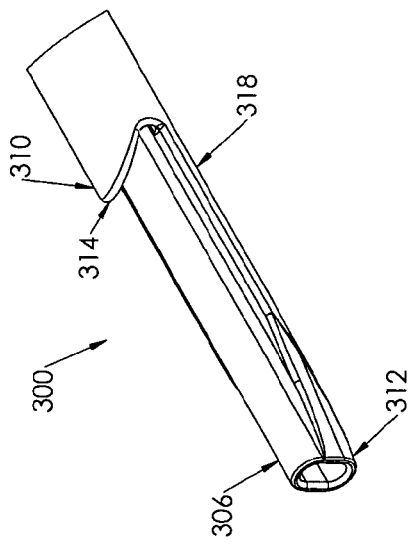
FIG. 6 is an enlarged perspective view of a distal tip of a catheter assembly according to a third preferred embodiment of the present invention.

A third embodiment of a distal end 306 of a catheter assembly 300 according to the present invention is shown in FIG. 6. The distal end 306 of the catheter assembly 300 is similar to the distal end 206 of the catheter assembly 200 as described above with respect to the second embodiment of the present invention, but a distal end 314 of a first lumen 310 tapers distally from a junction of the first lumen 312 and a support rib 318 to the distal end 314 of the first lumen 310.

Preferably, the catheter assemblies 200, 300 are constructed of the same material and by the same method as the catheter assembly 100 disclosed above. Further, the catheter assemblies 200, 300 may each include the hub 130, the ingrowth cuff 168, and the extension portion 104 as described above with respect to the catheter assembly 100.

Preferably, the catheter assemblies 100, 200, 300 are inserted into the patient through any known insertion technique, such as the Seldinger technique, although those skilled in the art will recognize that other methods may be used to inset the catheter assemblies 100, 200, 300.

The combination of the interior profile of the lumens 110, 112 and the symmetry of the hub 130 provide for a simple and cost effective molding process over other similar catheters known in the art.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A multi-lumen catheter assembly comprising:
   a catheter body having first and second lumens extending from respective distal openings at a distal catheter end to respective proximal openings at a proximal catheter end,
   the first lumen having a generally arcuate cross-section with a first generally rounded cross-section end and a second generally rounded cross-section end, the generally arcuate cross-section being defined between two opposing substantially parallel, arcuate and elongate sides extending between the first and second cross-section ends, and
   the second lumen having a generally oblong cross-section having a first generally rounded end and a second generally rounded end and first and second elongated opposing substantially straight sides and has a major axis parallel to the elongated opposing sides and extending between the first and second ends that is oriented radially with respect to the catheter and wherein at least a portion of the first end of the generally oblong cross-section of the second lumen is interposed directly between the first cross-section end and the second cross-section end of the first lumen.

2. The multi-lumen catheter assembly according to claim 1, wherein the catheter assembly has a generally round cross-section.

3. The multi-lumen catheter assembly according to claim 1, wherein the first lumen facilitates fluid flow in a first direction and the second lumen facilitates fluid flow in a second direction, opposite the first direction.

4. The multi-lumen catheter assembly according to claim 1, wherein the catheter has a geometric center, and wherein a portion of the second lumen encompasses the geometric center.

5. The multi-lumen catheter assembly according to claim 1, wherein the first lumen has a first distal end and the wherein the second lumen has a second distal end, extending distally of the first distal end.

6. The multi-lumen catheter assembly according to claim 5, further comprising an external reinforcing rib extending from the first distal end toward the second distal end along each side of the oblong distal end portion of the second lumen and extending laterally outwardly therefrom.

7. The multi-lumen catheter assembly according to claim 1, wherein the major axis generally bisects the first lumen.

8. The multi-lumen catheter assembly according to claim 1, wherein a ratio of the hydraulic radius of the second lumen to the hydraulic radius of the first lumen is between approximately 1.16 and 1.31.

9. The multi-lumen catheter assembly according to claim 1, wherein a ratio of the cross-sectional area of the second lumen to the cross-sectional area of the first lumen is between approximately 0.606 and 0.731.

10. The multi-lumen catheter assembly according to claim 1, wherein a ratio of the equivalent diameter ratio of the second lumen to the first lumen is between approximately 0.77 and 0.85.

11. The multi-lumen catheter assembly according to claim 1, wherein a centerline of the generally arcuate cross-section of the first lumen extends at least 180 degrees.

12. The multi-lumen catheter assembly according to claim 1, further comprising a first extension tube and a second extension tube, wherein the first and second extension tubes extend equi-angularly away from a longitudinal axis of the catheter assembly.

13. A multi-lumen catheter assembly comprising:
   an elongated cannulating body having a generally circular cross-section, wherein the body includes:
      a first lumen having a generally arcuate cross-section with a generally rounded first cross-section end and a generally rounded second cross-section end, the generally arcuate cross-section being defined between two opposing substantially parallel, arcuate and elongate sides extending between the first and second cross-section ends; and
      a second lumen having a generally oblong cross-section section having a first generally rounded end and a second generally rounded end and first and second elongated opposing generally straight sides and has a major axis parallel to the elongated opposing sides and extending between the first and second ends that is oriented radially with respect to the catheter and wherein at least a portion of the first end of the generally oblong cross-section of the second lumen is disposed generally centrally between the first generally rounded end and the second generally rounded cross-section end,
      wherein the first lumen has a distal opening at a first distal end and the wherein the second lumen has a distal opening at a second distal end, extending distally of the first distal end, and further comprising an external reinforcing rib extending from the first distal end toward the second distal end along each side of the oblong distal end portion of the second lumen and extending laterally outwardly therefrom.

14. The multi-lumen catheter assembly according to claim 13, wherein generally arcuate cross-section of the first lumen extends at least 180 degrees.

15. The multi-lumen catheter assembly according to claim 13, wherein the first lumen facilitates fluid flow in a first direction and the second lumen facilitates fluid flow in a second direction, opposite the first direction.

16. The multi-lumen catheter assembly according to claim 13, wherein the catheter has a geometric center, and wherein a portion of the second lumen encompasses the geometric center.

17. The multi-lumen catheter assembly according to claim 13, wherein the major axis generally bisects the first lumen.

18. The multi-lumen catheter assembly according to claim 13, wherein a ratio of the hydraulic radius of the second lumen to the hydraulic radius of the first lumen is between approximately 1.16 and 1.31.

19. The multi-lumen catheter assembly according to claim 13, wherein a ratio of the cross-sectional area of the second lumen to the cross-sectional area of the first lumen is between approximately 0.606 and 0.731.

20. The multi-lumen catheter assembly according to claim 13, wherein a ratio of the equivalent diameter ratio of the second lumen to the first lumen is between approximately 0.77 and 0.85.

21. The multi-lumen catheter assembly according to claim 13, further comprising a first extension tube and a second extension tube, wherein the first and second extension tubes extend equi-angularly away from a longitudinal axis of the catheter assembly.

* * * * *